United States Patent
Goebel et al.

(10) Patent No.: US 6,465,171 B1
(45) Date of Patent: Oct. 15, 2002

(54) CORT-PCR ASSAY FOR THE DISCRIMINATION OF ENDOGENOUS REVERSE TRANSCRIPTASE ACTIVITY IN EUKARYOTIC CELL LINES FROM INFECTIOUS RETROVIRUS CONTAMINATION

(75) Inventors: Scott Goebel, Ballston Spa, NY (US); Maurice Harmon, Tannersville, PA (US); Jim Tartaglia, North York (CA); William Lapps, Nazareth, PA (US); Francois Pelloquin, Lyons (FR); Dennis W. Trent, Carbonniers (FR)

(73) Assignee: Aventis Pasteur, Swiftwater, PA (US)

(*) Notice: Subject to any disclaimer, the term of this patent is extended or adjusted under 35 U.S.C. 154(b) by 148 days.

(21) Appl. No.: 09/594,075

(22) Filed: Jun. 14, 2000

Related U.S. Application Data
(60) Provisional application No. 60/138,973, filed on Jun. 14, 1999.

(51) Int. Cl.$^7$ .............................. C12Q 1/70; C12Q 1/68; C12P 19/34
(52) U.S. Cl. .............................. 435/5; 435/6; 435/91.1; 435/91.2
(58) Field of Search ................................ 435/6, 91.2, 5

(56) References Cited

U.S. PATENT DOCUMENTS

| | | | |
|---|---|---|---|
| 3,755,086 A | 8/1973 | Heimer | 195/103.5 R |
| 5,807,669 A | 9/1998 | Schüpbach et al. | 435/4 |

OTHER PUBLICATIONS

Pyra et al. Proc. Natl. Acad. Sci. USA 91(4): 1544–8.*
Weissmahr et al. J. of Virology 71(4): 3005–3012.*
Plotkin and Mortimer (1994) *Vaccines*, 2$^{nd}$ Edition, Philadelphia, PA. Saunders.
Who Expert committee on Biological Standardization (1999); Requirement for Biological Substances, No. 50. Geneva, Annex 1 *Who Technical Report Series*, No. 878, pp. 19–56.
Boni et al., (1996) *Clin. & Diag. Virol.* vol. 5, pp. 43–53.
Poiesz et al., (1980) *Proc. Natl. Acad. Sci.*, vol. 77, pp. 7415–7419.
Hoffman et al., (1985) *Virology*, vol. 147, pp. 326–335.
Silver et al., (1993) *Nucleic Acids Res.*, vol. 21, pp. 3593–3594.
Pyra et al., (1994) *Proc. Natl. Acad. Sci.*, vol. 91, pp. 1544–1548.
Boni et al., (1996) *J. Med. Virol.*, vol. 49, pp. 23–28.
Varmus and Swanstrom (1984) *RNA Tumor Viruses, Molecular Biology of Tumor Viruses*, vol. 2, 2$^{nd}$ edition, (New York, Cold Spring Harbor Laboratory) pp. 75–134.
Baltimore, (1970) *Nature*, vol. 226, pp. 1209–1211.
Weissmahr et al., (1997) *J. Virol.*, vol. 71, pp. 3005–3012.
Astrin et al., (1979) *Nature*, vol. 282, pp. 339–341.
Coffin et al., (1983) *Virology*, vol. 126, pp. 51–72.
Waters et al., (1972) *Science*, vol. 177, pp. 76–77.
Dunwiddie et al., (1986) *J. Virol.*, vol. 59, pp. 669–675.
Resnick et al., (1990) *J. Virol.*, vol. 64, pp. 4640–4653.
Boyce–Jacino et al., (1992) *J. Virol.*, vol. 66, pp. 4919–4929.
Bauer & Hofschneider, (1977) *Proc. Natl. Acad. Sci.*, vol. 73, pp. 3025–3029.
Bauer et al., (1977) *Eur. J. Biochem.*, vol. 79, pp. 345–354.
Bauer et al., (1978) *Biochim. Biophys. Acta.*, vol. 518, pp. 125–137.
Bauer et al., (1978) *Exp. Cel. Res.*, vol. 117, pp. 383–392.
Mandru and Peden, (1997) *J. Virol. Methods*, vol. 66, pp. 247–261.
Chang et al., (1997) *J. Virol. Methods*, vol. 65, pp. 45–54.
Lugert et al., (1996) *Biotechniques*, vol. 20, pp. 210–217.
Kahn et al., (1998) *J. Clin. Virol.*, vol. 11, pp. 7–18.
Robertson and Minor, (1996) *Biologicals*, vol. 24, pp. 289–290.
Tsang et al., (1999) *J. Virol.*, vol. 73, pp. 5843–5851.
American Academy of Pediatrics, (1999) Combination vaccines for childhood immunization: Recommendations fo the Advisory Committee on Immunization Practices (ACIP), the American Academy of Pediatrics (AAP) and the American Academy of Family Physicians (AFP). *Pediatrics*, vol. 103. pp. 1064–1068.
Limbach and Paoletti, (1996) *Epidemiol. Infect.* vol. 116, pp. 241–256.
Tartaglia et al., (1990) *Live recombinant viral vaccines. In: Immunochemistry of Viruses II, The Basis of Serrodiagnosis and Vaccines.* Van Regenmortel MHV, Neurath AR editors. (New York, Elsevier) pp. 125–151.
Heneine et al., (1995) *J. infect Dis.*, vol. 171, pp. 1210–1216.
Maudru and Peden, (1998) *J. Clin. Virol.*, vol. 11, pp. 7–18.
Purchase GH, Payne LN. Leukosis/Sarcoma Group (1984). In: Diseases of Poultry, 8$^{th}$ Edition, Hofstad et al., Editors, (Iowa State Press) pp. 360–405.

(List continued on next page.)

Primary Examiner—Carla J. Myers
Assistant Examiner—Alexander H. Spiegler
(74) Attorney, Agent, or Firm—McDonnell Boehnen Hulbert & Berghoff

(57) ABSTRACT

The present invention relates to the detection of the presence of reverse transcriptase enzymatic activity in eukaryotic cell lines. Specifically, the present invention comprises a method for discriminating between endogenous reverse transcriptase activity in a substrate cell line (e.g., avian) used as substrates for the manufacture of biological products (including viral vaccines) from exogenous infectious retrovirus by using a combination of transmissibility assay (viral replication) and PBRT assay (RT-PCR). Appropriate levels of viral amplification and number of PCR cycles are determined and employed that permit detection of exogenous infectious RT activity but not endogenous RT activity.

12 Claims, 3 Drawing Sheets

OTHER PUBLICATIONS

Dunwiddie et al., (1985) *Proc. Natl. Acad. Sci.*, vol. 82, pp. 5097–5101.

Robertson et al., (1997) *Biologicals,* vol. 25, pp. 403–414.

Fry and Loeb, (1986) *Animal Cell DNA Polymerases.* CRC Press Boca Raton.

Jones and Foulkes, (1989) *Nucleic Acids Res.*, vol. 17, pp. 8387–8388.

Persson et al., (1998) *Biologicals*, vol. 26, pp. 255–265.

Lovatt et al., (1999) *J. of Virological Methods*, vol. 82, pp. 185–200.

Cioffi et al., (1991) "A Rapid Quantitative Assay for Retroviral Reverse Transcriptase Activity." DNX, Athens, OH 45701.

Maudru et al., (1998) *J. of Clinical Verology*, vol. 11, pp. 19–28.

\* cited by examiner

CORT-PCR ASSAY FOR THE DISCRIMINATION OF ENDOGENOUS REVERSE TRANSCRIPTASE ACTIVITY IN EUKARYOTIC CELL LINES FROM INFECTIOUS RETROVIRUS CONTAMINATION

This application claims the benefit of U.S. Provisional Application No. 60/138,973 filed Jun. 14, 1999.

BACKGROUND OF THE INVENTION

1. Field of the Invention

The present invention relates to the detection of the presence of reverse transcriptase enzymatic activity in eukaryotic cell lines. Specifically, the present invention relates to a method for the discrimination of endogenous reverse transcriptase activity in avian cell lines used as substrates for the manufacture of biological products including viral vaccines from exogenous infectious retrovirus.

2. Summary of the Related Art

Of the commonly used viral vaccines licensed in the US, measles, mumps, yellow fever and influenza are produced in chicken cells derived from embryonated eggs (Plotkin and Mortimer (1994) Vaccines $2^{nd}$ Edition, Philadelphia, Pa., Saunders). Furthermore, cell substrates can be used for production of a variety of biological products, such as vaccines for hepatitis A, polio, and rabies as well as proteins, glycoproteins, and lipoproteins. The use of living cell substrates for the production of live attenuated virus provides the opportunity for infection of these cell lines by adventitious retroviruses. These live attenuated vaccines may act as vehicles for the transmission of different kinds of microorganisms or other undesired agents. The risk for inadvertent transmission is particularly high for live attenuated virus vaccine since they cannot be subjected to an inactivation procedure and most of them are injected into human, thus by-passing non-specific immune protection mechanisms. Thus, to ensure safety of vaccines for human use the cell substrates for vaccine production have been tested for the presence of replication-competent retroviruses that could be passed to human hosts during immunization (WHO Technical Report Series, 1994). Vaccines produced in continuous cell lines of any origin are required by experts in the field to be free of RT activity (Boni et al., (1996) Clin. & Diag. Virol. 5: 43–53.)

Avian cell lines are frequently used in the production of vaccines. Avian retroviruses classified within the ALSV subgroup E have been shown to be maintained in the germ line as endogenous virus (ev) loci and passed to progeny in a Mendelian fashion [16]. Chickens bred to be resistant to the ALSV subgroup E endogenous viruses (e.g., line-0 chickens), and therefore lacking ALV (ev) loci, have been shown to carry other germ line sequences, some of which are believed to be remnants of ancient proviral genomes. Another family of endogenous avian retroviruses of interest is referred to as (EAV-0) since they were first isolated from the (ev⁻) genome of line-0 chickens [17–20]. The EAV-0 loci have been shown to be highly expressed in embryonic cells derived from the avian genus, Gallus [21]. Moreover, these particles have been shown to contain RNA genomes with active RT-primer tRNA. Recent studies have shown that the particles from the EAV-0 endogenous retrovirus family are most likely responsible for a large portion of the particle-associated RT activity found in supernatants of cultured chick embryo fibroblasts [21]. Sequence analysis of several different EAV-0 isolates have indicated that a large deletion has occurred in the env gene which provides the scientific basis for and supports direct evidence for the replication incompetence of the particle-associated RT activity in cell culture [21].

Testing for the presence of retrovirus in cell substrates has been accomplished by assaying for the presence of reverse transcriptase (RT) activity based on the RNA-dependent synthesis of DNA (U.S. Pat. No. 3,755,086; Poiesz et al., (1980) Proc. Natl. Acad. Sci. USA, 77: 1415; Hoffman et al., (1985) Virology 147: 326). The RT enzyme or RNA-dependent DNA polymerase is essential for the establishment of the proviral state after infection of a cell and therefore is a mandatory component of the virus particle. Unfortunately, regardless of the templates and primers used, these RT assays are relatively insensitive compared to other more time-consuming assays for the detection of retroviruses such as cell culture or antigen detection methods. Attempts to detect uncharacterized retroviruses by the use of the polymerase chain reaction (PCR) with primers from conserved genomic regions have met with some success, but they lack the ability to assay for more than one infectious virus at a time, that is, the PCR test is not an open test. Furthermore, PCR will not detect the presence of unknown virus or viruses that have mutated in the region of the genome used for PCR amplification. PCR methods that utilize primers to specific retroviruses may not detect mutant variations of that virus if the mutation occurs in area to which the primers hybridize. Furthermore, PCR methods that utilize primers to specific retroviruses may require multiple and time consuming iterations to detect all possible retroviral species that may infect the substrate cell. Thus, both traditional RT assay and PCR based detection of retrovirus based on amplification of specific sequences are both relatively insensitive and can be time-consuming and difficult.

Recently, highly sensitive PCR based assays have been developed that can detect RNA-dependent DNA polymerase in the equivalent of one to ten particles (Silver et al. (1993) Nucleic Acids Res. 21: 3593–4; U.S. Pat. No. 5,807,669). One such assay, designated as PBRT (PCR-based reverse transcriptase), has been used to detect RT activity in a variety of samples (Pyra et al. (1994) Proc. Natl. Acad. Sci. USA 51: 1544–8; Boni, et al. (1996) J. Med. Virol. 49: 23–28). This assay is $10^6$–$10^7$ more sensitive than the conventional RT assay. In one instance PBRT was used to detect RT activity in live attenuated viral vaccines grown in chicken cells (Boni et al. (1996) Clin. Diag. Virol. 5: 43–53). The presence of RT activity in avian substrate cells where none had previously been detected is a potential source of concern since this activity may indicate the presence of a retrovirus that can potentially replicate in human cells. Thus, administration of a licensed viral vaccine may be the conduit for the inadvertent administration an adventitious retrovirus that can infect human cells and persist long-term as an integral part of the host genome. This is accomplished through the retroviral replication cycle that is characteristic of all retroviruses and depends in part upon the enzymatic activity of RT (Varmus and Swanstrom (1984) RNA Tumor Viruses, Molecular Biology of Tumor Viruses vol 2, $2^{nd}$ Edition, New York, Cold Spring Harbor Laboratory pp. 75–134; Baltimore (1970) Nature 226: 1209–11). Since retroviruses can be pathogenic in susceptible species, vaccines and other biological products for human use should be free of infectious retroviruses.

Alternatively, the presence of RT activity associated with cell substrates used in the production of viral vaccines may be due to low levels of RT-like activity associated with polymerases endogenous to the cell substrates. Moreover, it has recently been discovered that at least some of the RT activity associated with chicken cells used as substrates in the manufacture of live attenuated viral vaccines is associated with a particle that contains RNAs related to the EAV-0 family of retroviruses (Weissmahr et al. (1997) J. Virol. 71: 3005–12). Sequences of the EAV-0 family are prevalent in the genus Gallus and have been described as ancient proviral genomes (Dunwiddie et al. (1986) J. Virol. 59: 669–75); Resnick et al. (1990) J. Virol. 64: 4640–53; Boyce-Jacino et al. (1992) J. Virol. 66: 4919–29). Early studies using traditional RT assays had reported a particle-associated RT activity in the allantoic fluid of embryonated chicken eggs from retrovirus-free chickens and in concentrated medium of primary and secondary chicken embryo fibroblast cultures (Bauer & Hoffschneider (1977) Proc. Natl. Acad. Sci. USA 73: 3025–9; Bauer et al (1977) Eur. J. Biochem. 79: 345–54; Bauer et al. (1978) Biochim. Biophys. Acta 518: 125–37). No infectious retrovirus was found associated with the RT activity using avian target cells (Bauer et al. (1978) Exp. Cell Res. 117: 383–92).

Thus, utilizing the more sensitive PBRT assay testing of viral vaccine substrate cells for the presence of exogenous RT activity is problematic in that there is an increased incidence of false positive results due to the presence of endogenous RT activity. Several investigators have attempted to address the problem of false positives in the PBRT assay by modifying the assay conditions to decrease the RT activity produced by certain non-RT polymerases. Mandru and Peden (J. Virol. Methods, 66: 247–61 (1997)) were able to decrease the level of background RT activity produced by the RNA-dependent DNA polymerase activity of Taq polymerase by inserting a ribonucleotide digestion step prior to amplification of the cDNA product of the RT reaction by PCR and by using a thermostable DNA polymerase identified as having reduced RNA-dependent DNA polymerase activity. Chang et al. (J. Virol. Methods, 65: 45–54 (1997)) describe a PBRT assay in which the pH of the RT reaction was lowered, the incubation time of the RT reaction was decreased, and protease inhibitors were added to the RT reaction to decrease the RT activity of contaminating cellular polymerases. Lugert et al. (Biotechniques 20: 210–7 (1996)) describe a modified RT-PCR assay in which the amount of activated DNA was increased to inhibit the RT activity associated with endogenous polymerases but did not affect the RT activity of authentic RT molecules. None of the above referenced PBRT assays can distinguish RT activity from an adventitious retrovirus that may infect human cells from an endogenous RT source that is non-infectious, such as EAV-0.

Therefore, there exists a need for a screening method for RT activity in substrate cells that are used in the production of biological products, especially live attenuated virus for vaccines that can distinguish between non-infectious endogenous RT activity and RT activity associated with exogenous infectious retroviruses.

SUMMARY OF THE INVENTION

The present invention provides a method for detecting exogenous reverse transcriptase (RT) activity in a biological sample without interference from endogenous RT activity. This method is of particular use when the cellular substrate has a high level of endogenous RT activity (e.g., avian cells), making it impossible to assess the presence of contaminating infectious retroviruses based solely on the signature of RT activity. The present method achieves this by coupling an optimized transmissibility assay (for infectious retroviral amplification) with an optimized PBRT assay for detecting RT activity. The number of PCR cycles employed in the PBRT assay is selected to permit detection of the RT activity from the amplified exogenous retrovirus but not for detection of the lower level endogenous RT activity. The coupling of a retrovirus amplification process with PBRT is called Co-RT (CoRT) to reflect the coordination of the two assays.

Preliminarily, one determines the number of PCR cycles in the PBRT assay necessary to detect endogenous RT activity in a chosen cellular substrate permissive to retroviral infection, which substrate is to be used for exogenous infectious retrovirus amplification. Then, the transmissibility assay is employed to determine the amplification parameters required to yield an RT activity level greater than the endogenous RT activity of the cellular substrate and that can be detected with the PBRT assay using a number of PCR cycles that is less than the minimum required to detect endogenous RT activity of the cellular substrate. The degree of amplification necessary as determined by the transmissibility assay will, of course, depend both on the endogenous RT activity as well as on the initial level of exogenous infectious RT activity—the lower the level of exogenous infectious RT activity relative to the level of endogenous RT activity, the greater the amount of amplification necessary. For any particular amplification protocol, there will be a threshold level of detectable exogenous RT activity in the CoRT assay. The threshold level of exogenous infectious retrovirus detectable with a given set of CoRT assay parameters is that amount which after amplification yields an RT activity detectable by a number of PCR cycles in the PBRT assay that is at least one less than that required to detect endogenous RT activity.

Once the parameters for amplification from the transmissibility assay and detection from the PBRT assay have been determined, the CoRT assay according to the invention can be routinely and repeatedly conducted on biological samples of interest using those parameters. As demonstrated herein, the sensitivity achieved with 1.0 $TCID_{50}$ using the CoRT assay is similar to that achieved using the specific PCR assays.

The foregoing merely summarizes certain aspects of the invention and is not intended to limit the invention. All patents and other publications are hereby incorporated by reference in their entirety.

DETAILED DESCRIPTION OF THE PREFERRED EMBODIMENTS

Figure 1:
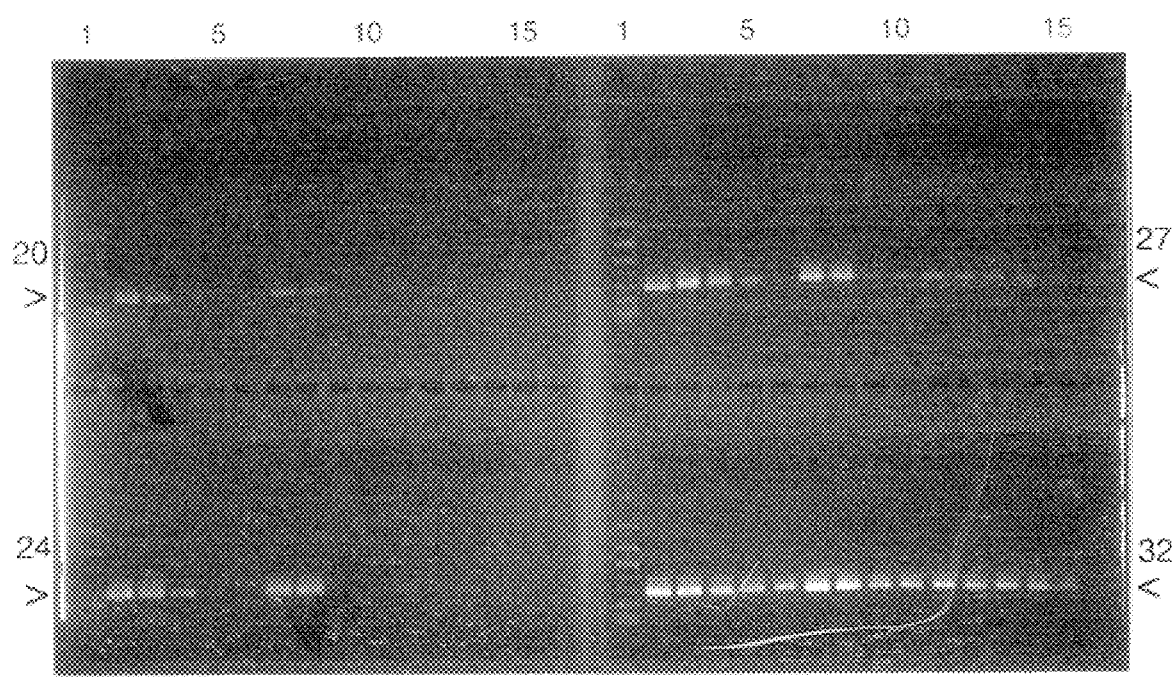
FIG. 1 shows the results of the comparative PBRT analysis using 20, 24, 27 and 32 cycles of PCR amplification.

The present invention comprises a method for detecting exogenous infectious retrovirus contamination in eukaryotic cell lines, particularly those used as substrates for the manufacture of biological products. Unlike prior art methods, the method of the invention is able to discriminate between endogenous RT activity and exogenous infectious retrovirus RT activity while retaining high sensitivity. This is accomplished by coupling an optimized transmissibility assay (for infectious retrovirus amplification) with a PBRT assay employing a predetermined number of PCR cycles, wherein the predetermined number of PCR cycles is sufficient to detect RT activity from amplified exogenous infectious retroviruses but insufficient to detect cellular substrate-endogenous RT activity.

An initial PBRT assay is first conducted to determine the minimum number of PCR cycles required to detect endogenous RT activity in a cellular substrate permissive to retrovirus infection. The assay is conducted with the substrate with a varying number of PCR cycles, and the minimum number of cycles required to detect the endogenous RT activity determined. As implied, the cellular substrate should be chosen to be permissive to infection from infectious retroviruses likely to be found in the biological sample of interest. Many cellular substrates are known in the art.

Then a transmissibility assay is employed using a known quantity of a known replication competent virus to determine, for a given threshold level of exogenous and endogenous RT activity, the amount of retrovirus amplification necessary to yield an infectious exogenous RT activity level in the cellular substrate that is detectable by a PBRT assay employing one or more fewer PCR cycles than is necessary to detect endogenous RT activity in the cellular substrate. One skilled in the art routinely adjusts the transmissibility assay parameters until the appropriate level of amplification is obtained.

The parameters determined from the initial PBRT assay and transmissibility assay can then be applied to a biological sample of interest to determine whether the sample has RT activity from an infectious retrovirus that is equal or greater than the threshold level. This is done by:

a) co-culturing the biological sample with a cellular substrate permissive to retroviral infection under conditions that permit retrovirus amplification, wherein infectious retrovirus present in the biological sample is amplified to yield a level of infectious retrovirus RT activity greater than the endogenous, non-infectious retrovirus RT activity of the cellular substrate;

b) subjecting the co-culture to a PBRT assay, wherein a number of PCR cycles is employed in the PBRT assay that is equal to or greater than the number required for detection of the exogenous, infectious RT activity in the co-culture but less than the number required for detection of the endogenous, non-infectious RT activity;

c) observing whether PCR-amplified nucleic acid is present in the co-culture subjected to the PBRT assay.

Definition of Terms

The term nucleotide refers to any ribonucleotide monophosphate and deoxyribonucleotide monophosphate with any natural or modified base in that structure that occurs as a component of a nucleic acid.

The terms rNTP and dNTP refer to a ribonucleotide triphosphate and deoxyribonucleotide triphosphate respectively with any natural or modified base. The terms rNTPs and dNTPs refer to a mixture of ribonucleotide triphosphate and deoxyribonucleotide triphosphate respectively with any natural or modified bases.

The term nucleic acid refers to a single-stranded or partly or completely double stranded oligomer or polymer. RNA consists entirely of ribonucleotide monophosphates and DNA consists entirely of deoxyribonucleotide monophosphates, however a nucleic acid may consist of both ribonucleotide monophosphates and deoxyribonucleotide monophosphates. The terms ss and ds characterize a nucleic acid as single-stranded and double-stranded respectively.

The term oligonucleotide refers to a single-stranded nucleic acid comprising at least between two and about 100 natural or modified nucleotides or a mixture thereof. The oligonucleotide can be derived from a natural nucleic acid or produced by chemical or enzymatic synthesis.

The term polynucleotide refers to a single-stranded nucleic acid comprising about 100 or more natural or modified nucleotides or a mixture thereof.

The terms upstream and downstream indicate the relative location within a nucleic acid; upstream indicating a direction toward the 5' end of the nucleic acid, downstream indicating a direction toward the 3' end of the nucleic acid.

The term reverse transcriptase (RT) refers to an enzyme which in its natural function, in a primer dependent reaction and by using dNTPs, synthesizes a DNA complementary to a template RNA.

The term reverse transcriptase activity refers to the activity of any enzyme by which in a primer-dependent reaction and by using dNTPs, synthesizes a DNA complementary to a template RNA.

The term primer refers to a nucleic acid of a sequence that is complementary to another nucleic acid. When hybridized to that nucleic acid, the primer, by means of its free 3'-OH group serves at a point at which the synthesis of a nucleic acid strand by an RT activity or a DNA-dependent DNA polymerase is initiated.

The term "RT primer" refers to the primer that exerts the function of a primer for RT activity.

The term "template nucleic acid" refers to the single-stranded nucleic acid to which, at least in part, a complementary DNA strand is synthesized by reverse transcriptase activity.

The term "template RNA" refers to those parts of the template nucleic acid that consists of RNA and to which at least in part a cDNA is synthesized.

The term "template DNA" refers to those parts of the template nucleic acid that consists of DNA.

The term cDNA refers to the nucleic acid the consist of DNA complementary to the template nucleic acid that has been synthesized by RT activity, as well as all the components of the RT primer.

RAV1, RAV2, and RAV0 refer to avian leukosis-sarcoma group, Rous-associated virus subgroups A, B, and E, respectively.

REV refers to a mammalian C-type virus, reticuloendotheliosis virus.

As used herein, the "transmissibility assay" refers to both (a) the initial assay to determine the amplification parameters necessary to yield a level of exogenous infectious RT activity detectable with a PBRT assay using fewer than the number of PCR cycles required to detect endogenous RT activity in a given cellular substrate as well as (b) the amplification portion of the CoRT assay using the parameters determined from the initial assay described in (a).

PBRT Assay

As indicated in the Background section, the PBRT assay is well known in the art, and any of the published protocols can be used (and modified as needed) by those of ordinary skill in the art as part of the CoRT assay of the present invention.

As used herein, the PBRT assay for RT activity comprises several steps. Initially a sample to be tested must be prepared. Suitable sample sources include cell lines from which live attenuated viral vaccine have or will be prepared, supernatant from cells used to produce live attenuated viral vaccine, and the live attenuated viral vaccine itself. After preparation of the sample to be tested, the sample is incubated in uninfected cell lines so that any exogenous virus will be amplified. The next step of the assay utilizes any RT activity in the sample to produce complementary DNA (cDNA) from an endogenous or exogenous RNA template. Production of cDNA utilizing the sample's inherent RT activity also requires a primer that is complementary to at least a portion of the RNA template. After production of the cDNA, this product is amplified by PCR (polymerase chain reaction). Multiple cycles of heating and cooling of the template DNA in conjunction with the appropriate primers and thermostable DNA-dependent DNA polymerase increase the number of cDNA molecules in a geometric progression. Finally the amplified DNA is identified and/or quantified.

Preliminarily, the threshold number of PCR cycles in the PBRT assay necessary to detect endogenous RT activity is determined. Multiple biological samples from a single source that is ostensibly free of infectious retrovirus are selected for assay with PBRT. As described herein, a variety of biological samples can be used. The biological samples are pre-treated to prepare the samples for PBRT assay. The RT reaction of the PBRT assay is then conducted under reaction conditions that have been optimized for the particular samples and primer-template combination selected. After treatment to remove the template nucleic acid, any cDNA produced in the RT reaction is then amplified by PCR with primers and reaction conditions chosen to optimize the PCR reaction. Each biological sample is run with varying numbers of PCR cycles to determine the level (if any) of PCR amplification required to obtain a positive result. The number of PCR cycles chosen is preferably between about 15 and about 35 cycles. After the PCR reaction is complete, the samples are subjected to a detection process in which it is determined whether any product from the PCR reaction is obtained. If product is obtained, the test is positive for RT activity (above a minimum detectable threshold); if no product is obtained, the test is negative for RT activity. Different numbers of PCR cycles should lead to results in which low numbers of cycles will yield negative RT activity results whereas higher numbers of cycles will yield positive RT activity results. These positive results are in fact "false-positives" in the sense that there is no exogenous infectious retrovirus present in the sample. The method of the present invention uses the differential results from the PBRT assay to define a threshold number of PCR cycles below which the RT activity from an endogenous non-infectious source of RT activity is undetectable. Fewer than this threshold number of PCR cycles can then be used to perform the CoRT assay in which any endogenous RT activity is not detected in test samples, but RT activity due to the presence of exogenous replicating retrovirus in the sample is detectable.

The number of PCR cycles required to discriminate between the sources of RT activity will vary according to the sample of interest as well as the sensitivity and selectivity of the templates and primers and conditions chosen for the RT and PCR portions of the CoRT assay. For example, in a sample where the endogenous background is very low, the number of PCR cycles can be greater than in a sample where the level of endogenous activity approaches that of an exogenous retroviral source of RT activity. The goal is to maximize the sensitivity and selectivity of the PBRT assay for infectious retrovirus without detecting harmless, non-infectious RT sources, thus decreasing false-positives.

For example, uninfected chicken embryo fibroblasts (CEF) were pre-treated and subjected to an optimized RT reaction using bacteriophage MS2 RNA template and RTC-1 primer. The template nucleic acid was digested using RNase and the samples were then subjected to PCR using 20, 24, 27 and 32 cycles. Portions of the PCR reaction were run on agarose gel and visualized with ethidium bromide. No product was seen in the samples subjected to 20 or 24 cycles, but product was seen in the samples subjected to 27 and 32 cycles. Therefore, the number of PCR cycles chosen for a CoRT assay for CEF should be less than 27 and is preferably between 20–26, more preferably between 24–26.

Decreasing the number of PCR cycles decreases the sensitivity of the PBRT assay. To compensate, the CoRT assay of the present invention uses viral amplification parameters during the transmissibility assay that ensures that the RT activity of exogenous, infectious retroviruses is above the background level of endogenous RT activity. The amplification is quantified through the use of replication competent control viruses.

Transmissibility Assay

The transmissibility assay and the amplification protocols employed are well known in the art, and published protocols can be routinely used (and modified) by those of ordinary skill in the art as part of the CoRT assay. Kahn et al, J. Clin. Virol. 1998; 11: 7–18; Robertson and Minor, Biologicals. 1996; 24: 289–90; Tsang et al., J. Virol. 1999; 73: 5843–51; Bauer et al., Biochim Biophy. Acta. 1978; 518: 125–37; and Bauer et al., Eur. J. Biochem. 1977; 79: 345–54.

Preliminarily, an initial transmissibility assay is conducted to determine the amount of amplification necessary for a given amount of retrovirus (and corresponding RT level) to permit detection of the RT activity by the PBRT assay employing less than the number of PCR cycles necessary to detect endogenous RT activity. The transmissibility assay can comprise incubation of positive control cells inoculated with infectious virus in the range of about 1 to $1 \times 10^5$ TCID$_{50}$. A negative control may also be utilized in the transmissibility assay of the present invention in which cells are inoculated with non-infectious virus in the range of about 1 to $1 \times 10^5$ TCID$_{50}$ and incubated. The length of incubation and other incubation conditions and parameters are adjusted for cell type as is known in the art, but the goal is to permit virus amplification in the control cells and in the sample cells as well if there is infectious retrovirus present. Preferably, the transmissibility assay is conducted with CEF, and the infectious virus is selected from RAV-1, RAV-2, or REV, the non-infectious virus is EAV-0, and the duration of the incubation is 7 days. CEF cells are used in the production of the live vaccines and are permissive to most known avian retroviruses. It is appropriate, therefore, to use them as the cell substrate for CoRT amplification. Endogenous RT levels were found to be quite consistent from assay to assay using numerous preparations of primary cells.

Supernatant from the first incubation is removed from both control and test samples and centrifuged to remove particulate matter. A portion of the supernatant is subjected to the PBRT assay as described herein and analyzed for the presence of PCR product. Cells from the positive and negative controls are treated to isolate genomic DNA. The genomic DNA can be obtained in a variety of ways know to the skilled artisan. A portion of this genomic DNA is subjected to PCR using primers that are specific for the virus of both the positive and negative control inoculum. The choice of primers and the PCR conditions for optimization of virus specific PCR are well-known to those of skill in the art. The PCR reaction is analyzed for the presence of PCR product. Optimally, the results of the specific PCR amplifications and the results of the RT-PCR (PBRT) assay will correlate. That is, a positive result in the specific PCR would also yield a positive result in the RT-PCR and a negative result in the specific PCR would also yield a negative result in the RT-PCR. Obviously this correlation depends on the level of initial viral infection and the number of PCR cycles used in the RT-PCR.

Multiple incubation periods can be used in the method of the present invention to increase amplification of the virus as needed. This is important in assessing the level of initial exogenous infectious retrovirus that can be detected using the CoRT assay. Just as the PBRT assay is preliminarily conducted on uninfected cells to establish the number of PCR cycles required to detect endogenous RT activity (as described above), the transmissibility assay is preliminarily conducted to determine the level of infectious retrovirus that can be detected by the assay using the cycling parameters determined in the RT-PCR (PBRT) portion of the assay. To determine the level of infectious retrovirus that can be detected from an initial infection one may have to perform multiple viral amplifications. After any incubation period, half of the volume of the control and test samples is transferred to another container having the same cell type as used in the first incubation. The specific PCR tests and CoRT assay can be run at the end of any or all incubation periods. Thus, the level of sensitivity of detection of the infectious retrovirus in the CoRT assay will depend on the amount of initial infectious retrovirus, the degree of viral amplification, and the selection of cycling parameters in the RT-PCR portion of the assay.

For example, in the CEF sample described herein, after 7 days of incubation the level of initial virus input that could be detected by the CoRT assay was 100 $TCID_{50}$ with RT-PCR using between 24–26 cycles. After an additional 7 days of viral amplification the level of initial virus input that could be detected by the CoRT was 1 $TCID_{50}$ under the same conditions. Therefore, selection of the number and length of viral amplifications will depend upon 1) the sensitivity desired and 2) the level of background endogenous RT activity. Thus, if background endogenous activity is high, the number of PCR cycles that can be run without detecting endogenous RT activity is less than if background endogenous RT activity is low. The lower the number of cycles, the less sensitive the assay for exogenous replicating retrovirus and the greater the need for increased viral amplification. In the method of the present invention the interplay between these two antagonistic factors is optimized so that exogenous replicating retrovirus is detected while endogenous RT activity is not.

As noted above, initially, a transmissibility assay is performed to determine the level of sensitivity of the RT-PCR, given the cycling constraints outlined above, that will not produce false negatives (the assay will detect exogenous infectious retrovirus present in samples). The results of the initial transmissibility assay enable one to determine the appropriate level of viral amplification to be used in combination with the RT-PCR test (i.e., PBRT) to produce the CoRT assay for a particular sample type and for a particular sensitivity.

The combination of appropriate viral amplification (transmissibility) and RT-PCR (PBRT) with the appropriate cycling parameters produces a CoRT test that provides sensitive detection of exogenous replicating retrovirus (no false negatives) without detection of endogenous RT activity (no false positives).

In the method of the present invention, specific PCR assays may initially be used in conjunction with the CoRT assay to verify the results obtained for the CoRT assay. Such specific PCR assays utilize the fact that specific viruses have unique genomes, a portion of which can be amplified by PCR if primers specific for those regions of the genome are selected. Thus, if a given replicating retrovirus is present in a given sample its genome will be detected by PCR specific for that virus. Conversely, if the retrovirus is not present detection of the virus by specific PCR will yield negative results. The CoRT assay of the present invention, however, does not require verification by specific PCR.

As previously described, the PBRT assay is conducted on a test sample that is of biological origin. The sample may be of human, animal or plant origin and includes both eukaryotic and prokaryotic cells. The following are examples of biological samples that can be tested in the PBRT assay:

Body tissues or organs of human or animal origin including (a) fluid tissues such as blood or blood fractions, e.g., serum, plasma, certain blood cell populations or fractions, blood products, e.g., blood proteins, coagulation factors, hyperimmune serum, antibody concentrates, hormones, etc.;

(b) firm tissues and organs such as transplantates, biopsy or autopsy material, smears taken from mucus membranes and other surfaces, single cells or preparations or extracts such as hormone preparations from glandular tissue, placenta, etc., meat and meat products from animals (c) Body fluids or excretions, both physiological or pathological, e.g., cerebrospinal fluid, urine, saliva, bile, sweat, milk, other glandular secretions, blister contents, amniotic fluid, synovial fluid, chamber fluid ascites or other effusions into body cavities, lymph, stools, etc., or products containing such materials.

(d) Samples of in vitro propagated prokaryotic and eukaryotic cell cultures of any kind as well as biological products made of any such e.g., vaccines, antibodies, growth and differentiation factors, hormones, recombinant proteins etc.

(e) Various materials, e.g., samples of food, water, and other beverages, environmental samples, hygiene samples, samples from useful plants (vegetables, fruit, wood, fiber plants).

Preferably, the sample comprises in vitro propagated eukaryotic cell cultures of any kind comprising, for example, vaccines, antibodies, growth and differentiation factors, hormones, recombinant proteins, etc. More preferably, the sample comprises chicken embryo fibroblasts, supernatant fluid from chicken embryo fibroblast cells, chicken embryos, chicken embryo fibroblast lysates, and allantoic fluid that are used in the preparation of live attenuated viral vaccines. Samples may be prepared by any conventional techniques known in the art used in preparing a test sample for RT activity testing. Such preparation steps include, but are not limited to, high speed centrifugation to remove cells, cell detritus, and other particulate contamination; ultracentrifugation for the pelleting of virus particles or for the adsorption of virus particles to a solid phase coated with antibodies or other suitable molecules or to another suitable carrier, or precipitation by means of immune reagents or chemical substances; ultrafiltration with filters of suitable pore size for the further elimination of contaminating particulate matter; and extraction of RT activity by means of a buffer containing a suitable detergent or other chemical or physical procedures protective of the enzyme.

In the CoRT assay of the present invention, the amplified sample is assayed for RT activity. The sample is pre-treated as described above so as to put the sample in a condition for the RT portion of the assay. For example, when the sample to be tested is media from cell substrates, the media is withdrawn from the cell substrates and centrifuged to remove particulate matter. Preferably, the pretreatment step should prevent inhibition of any RT activity and attempt to reduce background RT activity. A suitable sample volume is then transferred to a container for the RT portion of the CoRT assay.

A template-primer combination is required for the detection of RT activity. All template primer combinations used for the CoRT assay contain a heteropolymeric template nucleic acid. A segment of this, preferably immediately next to the 5' end of a hybridization sequence for a RT primer consists of RNA and is referred to as template RNA. The template RNA is the real substrate for RT activity; the synthesis of a DNA strand complementary to a template RNA defines the presence of RT or RT activity in the reaction mixture. The template nucleic acid usually consists of RNA from natural, recombinant or synthetic sources, however hybrid DNA/RNA sequences may also be used.

The template-primer combination is chosen so that the CoRT assay guarantees the maximum sensitivity and specificity for the detection of the retroelements. It is important to make sure that a nucleic acid amplification process is initiated only if during the reverse transcription of the template nucleic acid the piece of template RNA of sufficient length has been reversed transcribed. Furthermore, care must be taken to prevent the initiation of the amplification process by a nucleic acid in the sample that is independent of that synthesized during reverse transcription. It is important for the specificity and sensitivity of the CoRT assay that the template nucleic acid chosen is neither identical nor partially identical to any of the nucleic acids present in the sample, whether these be part of the normal genome of a species or a nucleic acid of an infectious agent or other contaminating nucleic acids whose presence may not be excluded in the sample.

In order to reach maximum specificity for the retroviral RT test, a heteropolymeric template RNA is preferred. In addition, the efficiency of cDNA synthesis by various types of enzymes with RT activity may be influenced, above all, by the processivity of these enzymes. Thus the template nucleic acid may be selected based on such considerations as secondary structure of the template nucleic acid. Preferably the template nucleic acid is bacteriophage MS2 RNA template.

In addition to the hybridization sequence used for the CoRT assay, most nucleic acid templates have at least one more hybridization sequence. When using reporter probes and whenever the hybridization sequence is exclusively used for the selection of the reporter probe, the template nucleic acid may contain several subsequent hybridization sequences, preferably separated from each other by spacer sequences. It thus becomes possible to hybridize several reporter probes.

All RT primers used in the assay are nucleic acids consisting of either partially or fully double-stranded or single-stranded RNA or DNA or a combination thereof. The primers comprise at least one hybridization sequence by which they hybridize to the template nucleic acid. It is possible that the RT primer may contain sequences that are not complementary to the template nucleic acid and are located upstream of the 3'-end of the hybridization sequence. The natural tRNA used as a RT primer in the replication cycle of retroviruses is an example of this kind of RT primer. In a particularly preferred embodiment of the present invention the RT primer RTC-1 (SEQ ID NO. 1: [(5'-d(GTAGTGCCACTGTTTCGTTTTG)-3']) is used.

In the CoRT assay of the present invention it may be necessary to produce, after the synthesis of the cDNA, a second DNA strand at least partially complementary to the cDNA. Therefore, at least one other nucleic acid, preferably a DNA oligonucleotide must be hybridized to the cDNA. This type of DNA comprises at least one hybridization sequence. In certain instances, at least one more functional sequence that is not complementary to the cDNA is added. On the second DNA strand this additional sequence will be located in the terminal position with regard to the hybridization sequence and thus be the equivalent of a flanking sequence. If these non-complementary sequences consist of DNA, they can be used for the introduction of either additional functional sequences needed but not yet present in the cDNA or other desired functions.

Reporter probes are nucleic acids used to demonstrate that a cDNA has been synthesized by binding, directly or indirectly, to the cDNA by means of hybridization. This binding may either be effected by directly hybridizing a hybridization sequence of the reporter probe to the hybridization sequence of the cDNA. In this case, the reporter probe is different from the template nucleic acid, with the exception of that sequence that is used for the hybridization to the cDNA. The reporter probe either represents or contains the nucleic acid to be amplified, or it or part of it is the educt of a further reaction or chain of reactions yielding the nucleic acid to be amplified.

The sensitivity of the CoRT assay is improved when optimal reaction conditions are chosen by monitoring the conditions in such reactions such as pH, salt conditions, ion concentration, primer concentration, template concentration, dNTP concentration. Optimization of such reaction conditions are within the purview of one of ordinary skill in this field of art.

In certain variants of the CoRT assay it is advantageous to remove the template nucleic acid from the reaction milieu prior to performing the PCR reaction to amplify the cDNA produced in the RT reaction. Measures for removal of the RNA include total degradation of the RNA contained in the reaction mixture by means of enzymatic treatment (RNase) or chemical treatment (base hydrolysis) without however removing the synthesized cDNA. The degradation of the RNA also destroys the function of the template nucleic acid since it necessarily contains a template RNA. It is also possible to append a carrier to the 5'-end of the RT primer such that upon subsequent synthesis of a cDNA molecule, the cDNA is through the RT primer attached to the carrier molecule. Thus, it is generally possible to eliminate the template nucleic acid by denaturing and subsequently washing it away.

After completion of the RT reaction the reaction mixture comprises cDNA produced from the reaction. In the next step of the CoRT assay of the present invention, the cDNA serves as a nucleic acid template for amplification by PCR.

The PCR primer combination is chosen so that the CoRT assay guarantees the maximum sensitivity and specificity for the amplification of the cDNA produced in the RT reaction. A nucleic acid amplification process should be initiated only if during reverse transcription of the template nucleic acid the piece of template RNA of sufficient length has been reversed transcribed. Furthermore, care must be taken to prevent the initiation of the amplification process by a nucleic acid in the sample that is independent of the cDNA synthesized during reverse transcription. It is important for the specificity and sensitivity of the assay that the primer combination chosen for PCR will not amplify the nucleic acids present in the sample whether these be part of the normal genome of a species or a nucleic acid of an infectious agent or another contaminating nucleic acids whose presence may not be excluded in the sample. Techniques for achieving the foregoing are well known and routinely used by those of ordinary skill in the art. Maudru and Peden, J. Virol. Methods. 1997; 66: 247–61; Chang et al., J. Virol. Methods. 1997; 65: 45–54; and Lugert et al., Biotechniques. 1996; 20: 210–17.

Multiple primers may be used to enhance specificity and sensitivity. Such multiple primer systems are often referred to as nested primers. In a system using nested primers, two primers are selected for use in the first several rounds of the PCR reaction. After completion of a number of rounds, one or two new primers (nested primers) that hybridize to the template interior to the initial primers are introduced into the PCR reaction for all subsequent rounds of amplification. The location of the site of hybridization of the nested primers on the PCR template nucleic produce a product that is shorter than the product produced by the primers chosen for the initial rounds of PCR.

Preferably, the RT primer RTC-1 is used in combination with RT-2 (SEQ ID NO. 10 5'-TCCTGCTCAACTTCCTGTCGAG-3').

Once the PCR reaction is complete, products of the PCR reaction (if any) are detected by appropriate means. For example the PCR products may be run on an agarose gel and visualized with ethidium bromide.

Once the optimization between transmissibility and cycling is determined, the CoRT assay can be run on any test sample with the pre-determined level of viral replication and number of PCR cycles during RT-PCR.

The absence of identifiable amplified DNA indicates that the level of RT activity in the sample is below the detection limit of the RT assay (approximately $10^{-9}$ U in general; approximately $10^{-7}$ U for avian cells) and is indicative of the absence of replicative infectious retrovirus as well as any other potential source of RT activity. The presence of identifiable DNA indicates the presence of RT activity in the sample and may be indicative of replicating infectious retrovirus. The PBRT assay does not distinguish among the potential sources of RT activity. The assay only indicates the presence or absence of RT activity above a certain level.

With respect to vaccine production, the stage of manufacture at which the CoRT assay is performed will depend on the method of manufacture of the viral vaccine. For example, viral vaccines manufactured from primary cell lines may need to be assessed on a lot by lot basis, whereas for viral vaccines manufactured from an established cell bank and viral seed it may be sufficient to test the cell bank(s) and viral seed(s). As previously stated with respect to CEF, the sample may comprise chicken embryo fibroblasts, supernatant fluid from chicken embryo fibroblast cells, chicken embryos, chicken embryo fibroblast lysates, and allantoic fluid that are used in the preparation of live attenuated viral vaccines.

EXAMPLES

Example 1

PBRT Assay

Sample Preparation

Clarified supernatant preparation from a biological sample co-incubated with CEF cells was diluted 1:10 in a buffer consisting of 50 mM Tris/HCL pH 8.0, 5 mM DTT, 50 mM KCL, 0.25 mMEDTA, 0.025% (w/v) triton X-100, 50% (v/v) Glycerol. Using this dilution, 10 µl was run in the assay.

Annealing

| | | |
|---|---|---|
| Template | MS2 RNA | 1.8 µg/Rx Stock solution 0.8 µg/µl |
| Primer | RT1C | 18 pmol/Rx Stock solution 50 pmol/µl |

Annealing Reaction Conditions

| Temperature | Time |
|---|---|
| 94° C. | 1 min. |
| 37° C. | 10 min. | cDNA Synthesis

1. The annealed primer/template was added to the Add 3 buffer and mixed well.
2. 18 µl of the Add 3 buffer annealed primer/template mix was aliquoted into PCR tubes.
3. 10 µl of the diluted test supernatant was added to the PCR tubes and mixed well. Add 3 buffer.

| Reagent | Volume |
|---|---|
| 1M Tris/HCl pH 8.0 | 14 µl |
| 1M KCl | 14 µl |
| 1M MgCl$_2$ | 2.2 µl |
| 1M DTT | 4 µl |
| 20 mg/ml BSA | 1.7 µl |
| 10% Triton-X100 | 10 µl |
| 25 mM dNTP | 10 µl |
| 5s rRNA 0.8 µg/µl | 108 µl | cDNA Reaction conditions:

| Temperature | Time |
|---|---|
| 37° C. | 60 min. |
| 95° C. | 5 min. |

MS2 RNA Degradation

1 µl of RNase (Boehringer Mannheim stock 10 mg/ml) was added to each reaction.

Reaction conditions:

| Temperature | Time |
|---|---|
| 37° C. | 30 min. |

PCR Amplification

75 µl of the Core mix was added to each reaction.

Core Mix:

| Reagent | volume |
|---|---|
| 10 x buffer | 75 µl |
| RT1C 50 pmol/µl | 2.8 µl |
| RT2 50 pmol/µl | 5.0 µl |
| TAG Polymerase 5 u/µl | 5.0 µl |

-continued

| Reagent | volume |
|---|---|
| DNTP mix 25 mM | 2.5 μl |
| distilled water | 657 μl |

Reaction conditions:

| Temperature | Time |
|---|---|
| 94° C. | 30 sec. |
| 56° C. | 30 sec. |
| 72° C. | 30 sec | number of cycles used: assay at 24 and 27

Example 2

Control RT-PCR Sensitivity Assay

To determine the sensitivity of the PBRT assay the following samples were subjected to the PBRT assay as described in Example 2 and 3 under a number of different amplification cycles:

| | Result (+/−) with # of PCR Cycles | | | |
|---|---|---|---|---|
| Sample | 20 | 24 | 27 | 32 |
| $5 \times 10^{-4}$ U AMV RT | + | + | + | + |
| $5 \times 10^{-5}$ U AMV RT | + | + | + | + |
| $5 \times 10^{-6}$ U AMV RT | − | + | + | + |
| $5 \times 10^{-7}$ U AMV RT | − | − | + | + |
| $5 \times 10^{-8}$ U AMV RT | − | − | − | + |
| $10^2$ TCID$_{50}$RAV1 | + | + | + | + |
| 1 TCID$_{50}$RAV1 | + | + | + | + |
| Uninfected CEF | − | − | + | + |
| Uninfected CEF | − | − | + | + |
| Uninfected CEF | − | − | + | + |
| Uninfected CEF | − | − | + | + |
| Uninfected CEF | − | − | + | + |
| Uninfected CEF | − | − | + | + |
| Blank | − | − | − | + |

Example 3

Specific PCR Assay for Retrovirus (Validation of CoRT)

The nucleotide sequences of the long terminal repeats (LTRs) in RAV1, RAV2, REV, EAV were reviewed to determine suitable primers for amplification of specific nucleotide sequences within these retroviruses. For both RAV1 and RAV2 three sequences were identified:

ALV1: SEQ ID NO.2:
5'-CTCTGCAATGCGGAATTCAGTGGT-3'

ALV2: SEQ ID NO.3:
5'-AGGGGGAAATGTAGTCTTATGCAAT-3'

ALVnest. SEQ ID NO.4:
5'-ATACTCTTGTAGTCTTGCAACATG-3'

For REV three sequences were identified

RevA1: SEQ ID NO.5:
5'-CATACTGAGCCAATGGTTGTAAAGGGCA-3'

RevA2: SEQ ID NO.6:
5'-AATGTTGTATCGAAATACTACGG-3'

Revnest2: SEQ ID NO.7:
5'-TTCAGTCCGGACCCCTACC-3'

For EAV two sequences were identified

Eav06: SEQ ID NO.8:
5'-ATAGGCGTGATCGGGGTCTCGGGATG-3'

Eav08: SEQ ID NO.9:
5'-AGCCTGCGGCTTGGCCAAATACCG-3'

1 μl of samples RAV1, REV, and EAV (described above) isolated genomic DNA from cells were transferred to PCR tubes containing 99 μl of a PCR mix (10 mM Tris-HCl, pH=8.3, 250 μM dNTPs, 0.5 U of Taq thermostable DNA polymerase (Amplitaq, Perkin-Elmer Roche Molecular Systems, Branchburg, N.J.). 0.25 μM of ALV1 and ALV2 were added to the RAV1 samples, 0.25 μM of RevA1 and RevA2 were added to the REV samples, and 0.25 μM of Eav06 and Eav08 were added to the EAV samples. PCR reactions were carried out on the REV and RAV1 samples at 94° C. for 1 min. and 20 cycles of 94° C. for 30s, 50° C. for 30s, and 72° C. for 30s, then 1 μl of PCR reaction mixture was added to a new tube containing the PCR mixture described above but 0.25 μM Revnest2 and 0.25 μM ALVnest replaced the REV and ALV primers in the REV and RAV1 samples, respectively. Nested PCR was carried out for an additional 5 cycles of 94° C. for 30s, 56° C. for 30s, and 72° C. for 30s followed by 72° C. for 10 min. PCR products were analyzed by 1.5% agarose gel electrophoresis stained with ethidium bromide. A positive PCR result for RAV1 yields a single band at 178 bp. A positive PCR result for REV yields a single band at 230 bp.

1 μl EAV samples were transferred to PCR tubes containing 99 μl of a PCR mix as described above. 0.25 μM of Eav06 and Eav08 were included in the PCR mix. PCR reactions were carried out at 94° C. for 1 min. and 28 cycles of 94° C. for 30s, 56° C. for 30s, and 72° C. for 30s, followed by 72° C. for 10 min. PCR products were analyzed by 1.5% agarose gel electrophoresis stained with ethidium bromide. A positive PCR result yields a single band at 178 bp.

| Sample | Primers | Result (+/−) |
|---|---|---|
| RAV1 $10^2$ TCID$_{50}$ | ALV1/ALV2/ALVnest | + |
| RAV1 1 TCID$_{50}$ | ALV1/ALV2/ALVnest | + |
| Rouvax 798 | ALV1/ALV2/ALVnest | − |
| Rouvax 798 + 1 RAV 1.0 TCID$_{50}$ | ALV1/ALV2/ALVnest | + |
| Rouvax 800 | ALV1/ALV2/ALVnest | − |
| Rouvax 800 + 1 RAV 1.0 TCID$_{50}$ | ALV1/ALV2/ALVnest | + |
| Rouvax 801 | ALV1/ALV2/ALVnest | − |
| Rouvax 801 + 1 RAV 1.0 TCID$_{50}$ | ALV1/ALV2/ALVnest | + |
| Uninfected CEF | ALV1/ALV2/ALVnest | − |
| RAV1 $10^2$ TCID$_{50}$ | ALV1/ALV2/ALVnest | − |
| REV $10^3$ TCID$_{50}$ | REVA1/REVA2/REVnest | + |
| Rouvax 798 | REVA1/REVA2/REVnest | − |
| Rouvax 798 + 1 RAV 1.0 TCID$_{50}$ | REVA1/REVA2/REVnest | − |
| Rouvax 800 | REVA1/REVA2/REVnest | − |
| Rouvax 800+ 1 RAV 1.0 TCID$_{50}$ | REVA1/REVA2/REVnest | − |
| Rouvax 801 | REVA1/REVA2/REVnest | − |
| Rouvax 801+ 1 RAV 1.0 TCID$_{50}$ | REVA1/REVA2/REVnest | − |
| Uninfected CEF | REVA1/REVA2/REVnest | − |
| RAV1 $10^2$ TCID$_{50}$ | Eav06/Eav08 | + |
| RAV1 1 TCID$_{50}$ | Eav06/Eav08 | + |
| REV $10^3$ TCID$_{50}$ | Eav06/Eav08 | + |
| Rouvax 798 | Eav06/Eav08 | + |
| Rouvax 798 + 1 RAV 1.0 TCID$_{50}$ | Eav06/Eav08 | + |
| Rouvax 800 | Eav06/Eav08 | + |
| Rouvax 800+ 1 RAV 1.0 TCID$_{50}$ | Eav06/Eav08 | + |
| Rouvax 801 | Eav06/Eav08 | + |
| Rouvax 801 + 1 RAV 1.0 TCID$_{50}$ | Eav06/Eav08 | + |

Example 4

Transmissibility Assay

Preparation of Primary Chick Embryo Fibroblast Monolayers

Primary chicken embryo fibroblasts (Select Laboratories) were even mixed by gentle agitation and 15.9 ml removed and poured into a sterile funnel filter wrapped with 18 layers of cheesecloth. The run through was collected in a 250 ml conical centrifuge tube. The volume of the suspension in the centrifuge tube was doubled by the addition of media (DMEM 2% NCS). The suspension was centrifuged (200 g) for 10 min. at 4° C. (1000 rpm in Beckman GPKR) to collect the red blood cells. The supernatant was transferred to another 250 ml conical centrifuge tube and centrifuged (850 g) for 15 min. at 4° C. (2000 rpm in Beckman GPKR) The pellets from both centrifugations were the resuspended (without disturbing the RBC pellet) and 12 ml of the re-suspension was transferred to a 50 ml sterile tube to disperse the cells, then this suspension was pooled with the final cell suspension, streaked on TSA II and Sabourand Dextrose plates. The cells were then resuspended in CEF media. A 1:10 dilution of cells in CEF media was made and an additional 1:10 made in 0.2% trypan blue. The viable cells were then counted with a hemacytometer. Cells were then diluted to a density of $2.5 \times 10^6$ cells/ml and dispensed into a 35 mm plate.

Control Inoculations

For control experiments 35 mm plates of sub-confluent primary CEF cells (approximately $1.6 \times 10^6$ cells) in 2 ml of media (DMEM with 10% NCS) were inoculated with 1 to $10^5$ $TCID_{50}$ of one type of avian retrovirus stock that has been diluted in 1 ml to the desired concentration in DMEM with 2% NCS (DMEM with 4 mM glutamine, 1 mM sodium pyruvate, 1% antibiotic/antimycotic (Gibco), 2% NCS). After inoculation 1 ml of media supplemented with 8 µg/ml DEAE-Dextran was added to the plates and the plates were then incubated overnight at 37° C. After overnight incubation the inoculum was removed and fresh media (DMEM 2% NCS) was added and the plates incubated for 7 days at 37° C. After 7 days, 1 ml of supernatant of the plate was transferred to fresh 35 mm plates containing CEF cells as described above. 1 ml of media supplemented with 8 µg/ml DEAE-Dextran was added to the plates and incubated overnight at 37° C. After overnight incubation the inoculum was removed and fresh media (DMEM 2% NCS) was added and the plates incubated for 7 days at 37° C.

Test Article Inoculations

The supernatant from measles vaccine cell cultures, ALVAC construct cell culture or allantoic fluid from an influenza virus challenge preparation were harvested and 1 ml of harvest was used to inoculate sub-confluent primary CEF cells (approximately $1.6 \times 10^6$ cells) in 2 ml of media (DMEM with 10% NCS) in the presence and absence of 1.0 $TCID_{50}$ of RAV1. After inoculation 1 ml of media supplemented with 8 µg/ml DEAE-Dextran was added to the plates and the plates were then incubated overnight at 37° C. After overnight incubation the inoculum was removed and fresh media (DMEM 2% NCS) was added and the plates incubated for 7 days at 37° C. After 7 days, 1 ml of from the supernatant of the plate was transferred to fresh 35 mm plates containing CEF cells as described above 1 ml of media supplemented with 8 µg/ml DEAE-Dextran was added to the plates and incubated overnight at 37° C. After overnight incubation the inoculum was removed and fresh media (DMEM 2% NCS) was added and the plates incubated for 7 days at 37° C.

RT-PCR Assay of Test Article Inoculations 1 ml of culture supernatant was removed from the cell cultures and placed in a 1.5 ml microfuge tube. The supernatant was centrifuged at 13000 rpm for 5 min. The supernatant from the centrifugation was decanted from cellular debris and stored at −80° C. The supernatants were subjected to the PBRT assay as described in Examples 1 and 2.

Specific PCR Assay

The supernatant was removed from the CEF monolayers in the 35 mm plate and 1 ml PBS without Mg/Ca was added. The cells were scraped from the plate and resuspended by repeated pipetting and transferred to a 1.5 ml microfuge tube. Cells were briefly spun in a microfuge to bring the cells into a pellet. The supernatant was discarded and the cell pellet was resuspended in 0.2 ml PBS without $Mg^{2+}/Ca^{2-}$. The genomic DNA from the CEF was purified using a Qiagen Blood Kit (Qiagen) according to the instruction on pages 15–17 of the instruction booklet (Blood and body fluids). 1 µl (approximately 0.3–0.5 µg) of genomic DNA was added to 99 µl PCR mix with ALV primers and subjected to PCR as described in Example 5.

Below is a comparison of the results of the PBRT assay and the specific PCR assay with respect to the detection of a PCR product on 1.5% agarose stained with ethidium bromide.

| Sample | Source | Added Retrovirus | PBRT Result | PCR Result |
|---|---|---|---|---|
| Flu E-361 | Influenza | | − | − |
| Flu E-361 | influenza | RAV1 (1.0 $TCID_{50}$) | + | + |
| vCP325-01 | ALVAC | | − | − |
| vCP325-01 | ALVAC | RAV1 (1.0 $TCID_{50}$) | + | + |
| vCP325-02 | ALVAC | | − | − |
| vCP325-02 | ALVAC | RAV1 (1.0 $TCID_{50}$) | + | + |
| vCP1521-02c | ALVAC | | − | − |
| vCP1521-02c | ALVAC | RAV1 (1.0 $TCID_{50}$) | + | + |
| vCP1521-02a | ALVAC | | − | − |
| vCP1521-02a | ALVAC | RAV1 (1.0 $TCID_{50}$) | + | + |
| vCP1521-03c | ALVAC | | − | − |
| vCP1521-03c | ALVAC | RAV1 (1.0 $TCID_{50}$) | + | + |
| Rouvax 804 | Measles | | − | − |
| Rouvax 804 | Measles | RAV1 (1.0 $TCID_{50}$) | + | + |
| Rouvax 805a | Measles | | − | − |
| Rouvax 805a | Measles | RAV1 (1.0 $TCID_{50}$) | + | + |
| Rouvax 805b | Measles | | − | − |
| Rouvax 805b | Measles | RAV1 (1.0 $TCID_{50}$) | + | + |
| Rouvax 806 | Measles | | − | − |
| Rouvax 806 | Measles | RAV1 (1.0 $TCID_{50}$) | + | + |
| Rouvax 807a | Measles | | − | − |
| Rouvax 807a | Measles | RAV1 (1.0 $TCID_{50}$) | + | + |
| Rouvax 807b | Measles | | − | − |
| Rouvax 807b | Measles | RAV1 (1.0 $TCID_{50}$) | + | + |
| Uninfected cells | CEF | | − | − |
| Blank | Buffer | | − | − |

The experiment was repeated using RAV2 and the results were similar.

Discussion

Figure 2:
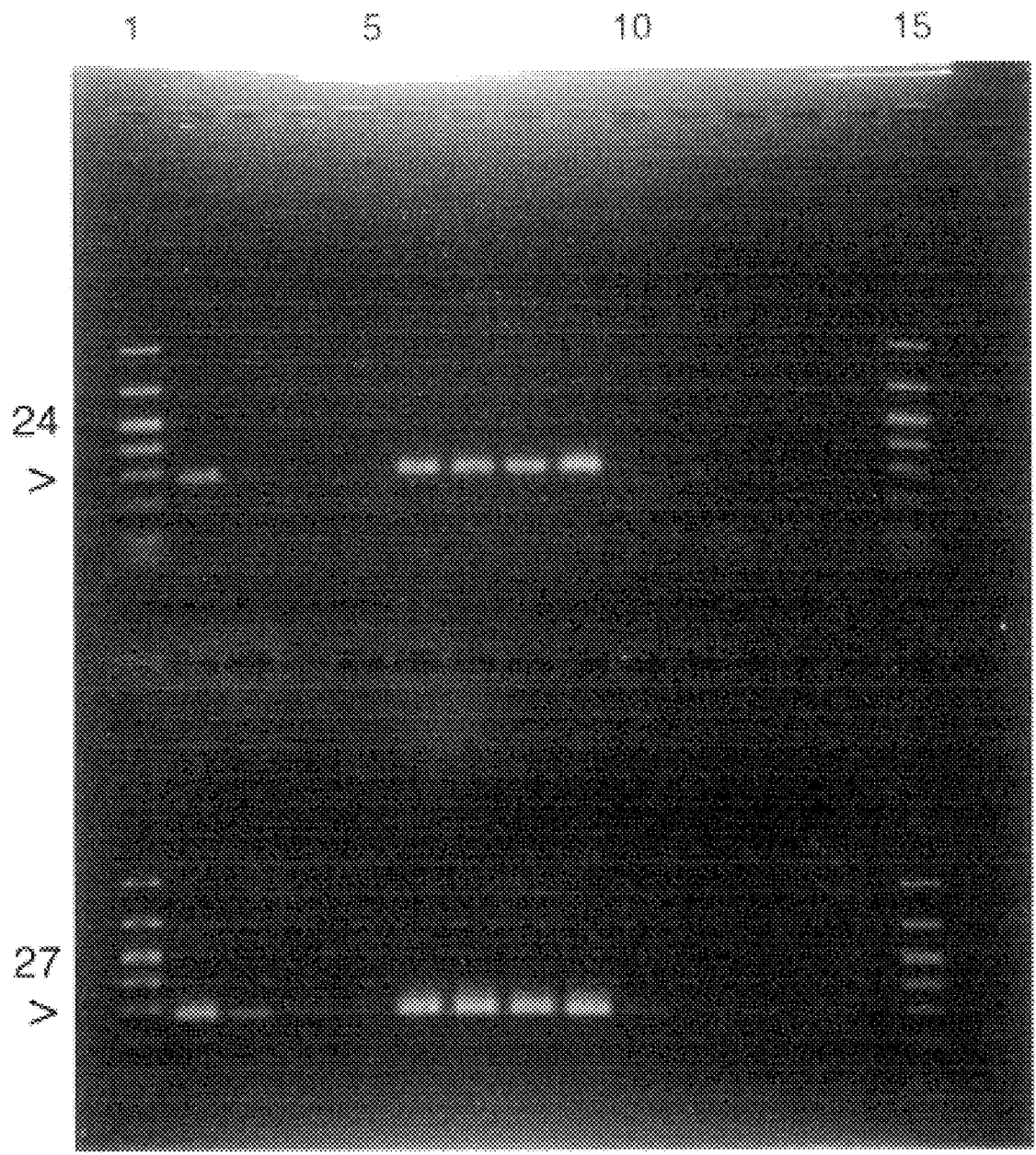
FIG. 2 shows the results of an initial transmissibility assay to determine the amount of detectable RT activity in a biological sample for a given set of parameters and PCR cycles.
Figure 3:
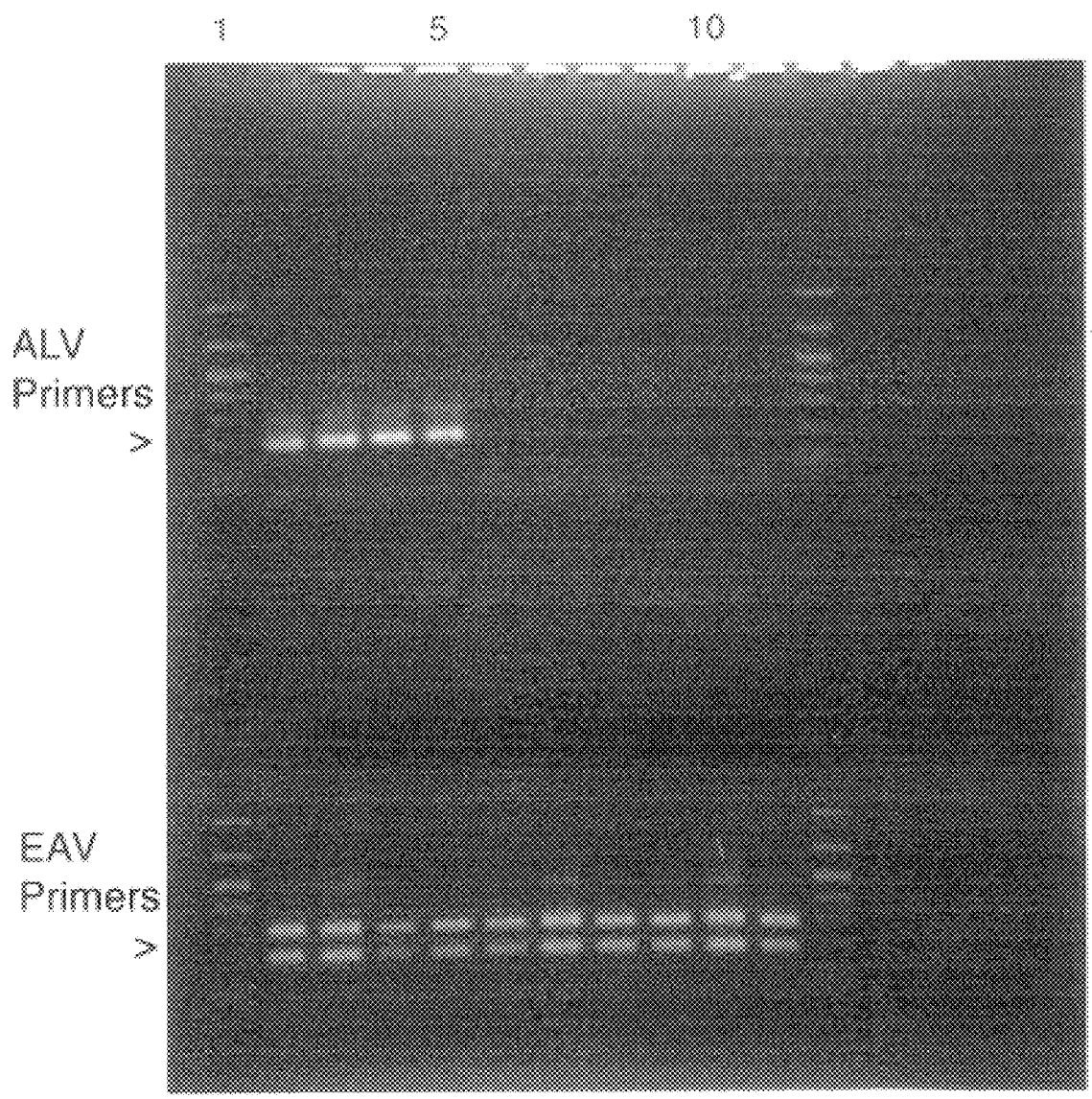
FIG. 3 displays the results of specific PCR analysis was used to confirm the CoRT analysis.

The results of the foregoing Examples are further illustrated in FIGS. 1–3.

FIG. 1 shows the results of the comparative PBRT analysis using 20, 24, 27 and 32 cycles of PCR amplification. Following CoRT analysis, RT activity is detected by assessing 20 µl of each PBRT reaction on a 1.5% agarose gel. Positive reactivity is indicated by the presence of a specific PCR product at 242 bp (arrow). In this experiment, assay sensitivity, defined in units of AmvRT detected, was compared to selectivity, the ability to quantitatively differentiate between cellular endogenous RT activity and RT activity associated with active exogenous retrovirus replication. Using limited PCR amplification steps of 20, 24, 27 and 32 cycles (as indicated) assay sensitivity increases with cycle number, but selectivity is lost with over-amplification at more than 24 cycles of PCR amplification. Lanes 1–15 represent the same samples at the indicated level of PCR amplification. Lane 1 marker lanes (2–6) buffer samples spiked with of $5\times10^{-4}$, $5\times10^{-5}$, $5\times10^{-6}$, $5\times10^{-7}$, and $5\times10^{-8}$ units of AmvRT, lanes (7 and 8) CEF cells infected with RAV1 at $10^2$ and 1.0 $TCID_{50}$ respectively lanes (9–14) from uninfected CEF and lane 15 negative buffer control for Taq Polymerase RT-like activity.

FIG. 2 shows the results of an initial transmissibility assay to determine the amount of detectable RT activity in a biological sample for a given set of parameters and PCR cycles. Following the cell culture portion of the CoRT assay RT activity is assessed by running 20 $\mu$l aliquots of each PBRT reaction on a 1.5% agarose gel. Positive reactivity is indicated by the presence of a 242 bp specific PCR product (arrows). The following samples were assessed for RT activity after 24 cycles (Top) and 27 cycles (bottom) of PCR amplification. Marker lane (1); buffer plus $5\times10^6$ uAmvRT lane (2); Buffer plus $5\times10^7$ uAmvRT lane (3); test article without spikes (i.e., without added retrovirus) lanes (4 and 5); test article plus RAV1 spike $10^2$ TCID 50 lanes (6 and 7); test article plus RAV1 spike 1.0 $TCID_{50}$ lanes (8 and 9); test article plus irradiated RAV1 spike $10^2$ $TCID_{50}$ lanes (10 and 11); control CEF lanes (12 and 13); buffer sample minus RT lane (14); marker lane (15).

FIG. 3 displays the results of specific PCR analysis used to confirm the CoRT analysis. Genomic DNA was prepared from the CEF cultures used in the transmissibility assay. Template DNA samples used for PCR amplification are as follows: marker lane (1); test article plus RAV1 spike of $10^2$ TCID-50 lanes (2 and 3); test article plus RAV1 spike 1.0 $TCID_{50}$ lanes (4 and 5); test article plus irradiated RAV1 spike of $10^2$ $TCID_{50}$ spike lanes (6 and 7); test article no spike lanes (8 and 9); control CEF cultures lanes (10 and 11); marker lane (12). Top set of the PCR reactions were performed with the ALV specific primer pairs, indicated by (ALV primers). Positive reactivity from samples lanes (2–5) is indicated by the presence of the specific 177 bp product. The bottom set of PCR reactions were performed with the EAV0 specific primer pair indicated by (EAV primers) used for positive template controls. The highly redundant nature of EAV0 and similarity to ALV(ev) loci leads to the amplification of several products found in all samples indicating all contained amplifiable DNA.

To develop the CoRT assay using primary CEF's in the transmissibility assay it was necessary to determine the baseline (endogenous) level of RT activity associated with the supernatant from cultured CEFs. Results of the comparative PBRT analysis using 20, 24, 27 and 32 cycles of PCR amplification are shown in FIG. 1. The four panels represent the same order of samples, with the indicated level of PCR amplification. The data in FIG. 1, lanes 2–6 represent buffer samples spiked with purified AMV RT. As expected, a quantitative, direct correlation was observed between assay sensitivity and the number of PCR cycles. By increasing PCR cycles from 20 to 27, assay sensitivity increased by 100 fold, as defined of units of AmvRT detected (FIG. 1 lane 3 at 20 cycles and lane 5 at 27 cycles). More importantly, by comparing the clarified supernatant samples prepared from CEF cells infected with the avian retrovirus RAV1 (FIG. 1 lanes 7 and 8) to clarified supernatants prepared from uninfected CEF's incubated for the same period of time (FIG. 1; lanes 9–14) we were able to define cycling parameters to address both, sensitivity and the ability to quantitatively discriminate between the level of RT activity inherent to the cells and that associated with exogenous replicating viruses. Samples from the exogenous retrovirus infected CEF cultures have RT activity detectable by 20 cycles of amplification (FIG. 1 lanes 7 and 8). In contrast samples from uninfected cultures (FIG. 1 lanes 9–14) required 27 cycles of amplification to detect a significant product band. Controlled PCR amplification, therefore provided a true differential between RT activity associated with retrovirus-spiked and uninfected control samples. At 32 cycles of PCR amplification, all samples had positive reactivity including the control (FIG. 1 lane 15 at 32 cycles) for RT-like activity from Taq polymerase. These results for 32 cycles of amplification are consistent with significant PCR over-amplification.

The level of amplification at which the supernatants in the uninfected samples become positive for RT activity defined both the baseline for endogenous RT activity in cultured CEF and the limit of the PBRT component of the CoRT assay sensitivity in cultured CEF cells. The sensitivity achieved at 27 cycles of PCR amplification was $5\times10^{-7}$ units of AmvRT (FIG. 1 lane 5). Therefore, using CoRT to detect the presence of exogenous virus from primary CEF supernatants, it was critical to limit the level of PCR amplification below 27 cycles to remain below the threshold of endogenous RT activity. Considering both sensitivity and selectivity in the CoRT assay, the optimal level of PCR amplification selected for the subsequent development of the PBRT detection was 24 cycles. Importantly, after 24 cycles of amplification the RT-like activity from Taq Polymerase remained below detection as represented by the buffer sample containing all reagents minus any RT source (FIG. 1 lane 14). Having established controls for both endogenous CEF RT activity and RT activity associated with Taq Polymerase, the positive reactivity from the CEF cultures containing exogenous virus was attributed solely to RT activity expressed by replicating, exogenous viral particles.

Limits of Detection by CoRT Assay

After 24 cycles of PCR amplification, the sample prepared from CEF cells infected with as little as 1.0 $TCID_{50}$ (FIG. 1 lane 8) of the avian retrovirus RAVi had positive reactivity by PBRT analysis. This indicated that as little as 1.0 infective dose of a replication competent virus was capable of being amplified to a level such that the associated RT activity was detectable above that of uninfected control samples. Following 24 cycles of PCR amplification, the detected product from both samples containing exogenous RT activity (FIG. 1 lanes 7 and 8) had a signal equivalent in intensity to that seen with $5\times10^{-6}$ units of AmvRT (FIG. 1 lane 4) or about $9\times10^5$ molecules AmvRT. This level of activity is significantly above the required threshold of $5\times10^{-7}$ units or $9\times10^4$ molecules of AmvRT in samples containing only endogenous RT activity (FIG.1 lanes 9–14) and allows for the discrimination between exogenous and endogenous activity. The level at which the endogenous activity is detected in our PBRT detection assay correlates well with the level of RT activity reportedly expressed from EAV0 (21). Consequently for test articles to have a positive reactivity in the CoRT assay employing CEF cells, they must have an associated level of virus that upon amplification the resultant RT activity is greater than the cellular endogenous threshold of $5\times10^{-7}$ units of AmvRT. The ability to detect that level of a replication competent virus within the significant RT background of cultured CEF is due to specific amplification of infectious viral particles during the cell culture transmissibility portion of the CoRT assay.

Product Testing Using the CoRT Assay

Using the CoRT assay we have tested numerous uninfected control cell retention lots (cell supernatant harvests) from vaccine production batches. The test articles were assessed by incubating 1 ml of the test article with or without a spike of a qualified lot of avian retrovirus (RAV1) on primary CEF as described in the materials and methods. Following the incubation period the PBRT detection assay was used to assess RT activity from the clarified supernatant samples. Representative data are presented in FIG. 2. Samples were subjected to either 24 cycles (top portion) or 27 cycles of PCR amplification (bottom portion). As expected following 24 cycles of PCR amplification the assay provided a sensitivity of $5\times10^{-6}$ units of AmvRT (FIG. 2; lane 2). The test articles were controlled by adding a spike of a replication competent avian retrovirus RAV1 to determine whether they contained RT inhibiting factors. Samples of test articles containing spikes of $10^2$ $TCID_{50}$ (FIG. 2; lanes 6 and 7) and 1.0 $TCID_{50}$ (FIG. 2; lane 8 and 9) of RAV1 had positive reactivity in the PBRT assay, indicating the absence of inhibitory factors. Test articles spiked with similar levels of irradiated RAV1 (FIG. 2; lanes 10 and 11) or unspiked samples demonstrated no reactivity after 24 cycles of PCR amplification (FIG. 2; lanes 4 and 5). After 24 cycles of PCR amplification, the uninfected controls for CEF endogenous RT activity, (FIG. 2; lanes 12 and 13) as well as the buffer sample (FIG. 2; lane 14) were negative indicating positive reactivity was not the result of endogenous cellular RT or Taq Polymerase associated RT-like activity.

When the level of PCR amplification was increased to 27 cycles (FIG. 2; bottom portion) the sensitivity of the assay was $5\times10^{-7}$ units of AmvRT (FIG. 2; lane 3). However, all samples of CEF cultures without exogenous virus spikes that were negative at 24 cycles became weakly positive at 27 cycles, having now achieved the level of sequence amplification necessary to detect the cellular endogenous RT activity (FIG. 2; lanes 4 and 5 and 10–13). The results of all the PBRT assays have been found to be highly reproducible and at 24 cycles of amplification the achieved assay sensitivity was $5\times10^{-6}$ units of AmvRT. Using positive viral spikes of 1.0 $TCID_{50}$ qualifies the level of detection with the CoRT assay to as low as 1.0 infective dose of a replication competent retrovirus. All articles tested to date have been negative for exogenous RT activity, with no indication of assay inhibition.

Samples prepared from the cell culture assays were assessed for the presence of infectious replicating retroviruses. Cell culture supernatants were assessed for enhanced RT activity using the PBRT assay, while cellular genomic DNA was assessed for integrated provirus using a specific PCR assay. All test articles that were spiked with infectious virus were positive by the PBRT assay and for integrated provirus by specific PCR. Enhanced RT activity was suggestive of replication while the finding of integrated provirus confirmed the replication and amplification of the viral spike in the presence of the test article in the co-culture transmissibility assay. The fact that the UV irradiated virus spikes failed to give a positive result in either the PBRT or PCR assay further supports the conclusion that viral replication is necessary to give positive results with the CoRT assay. The negative results from the unspiked test articles for either enhanced RT activity or integrated provirus, demonstrated the lack of a detectable replicating adventitious retrovirus within any of the test articles. While we present the specific PCR data to confirm the CoRT analysis, the narrow scope of specific PCR testing limits the utility of such assays for product or substrate testing and further supports the development of broad based assays such as the CoRT assay.

Confirmation of the Results of the CoRT Assay Using Retrovirus Specific PCR Assays In order to confirm the results obtained with the CoRT assay, a series of retrovirus specific PCR assays have been developed that target integrated genomic provirus elements. These assays have been developed to also distinguish exogenous retrovirus proviral sequences from those of endogenous proviral elements. When developing specific primers for exogenous ALV viruses it is essential to consider that all CEF cells carry germline ALV endogenous (ev) loci sequences unless the cells are obtained from chicks specifically bred to be resistant to ALV subgroup E viruses [28]. Sequence analysis comparing ALV exogenous and endogenous virus groups indicate sequence divergence within the LTR U3 region [29]. Oligonucleotide primers specific to the U3 region were used to amplify a 177 bp fragment from the exogenous provirus element. Cellular genomic DNA was prepared from the monolayer of the same cultures from which the clarified supernatants were prepared in order to maintain a correlation between the two different assay systems. Using the specific PCR assay for ALV exogenous viruses (FIG. 3 top row samples) we obtained positive RT activity with the test article samples spiked with the RAV1 virus at a level of $10^2$ $TCID_{50}$ (FIG. 3; lanes 2 and 3) and 1.0 $TCID_{50}$ (FIG. 3; lanes 4 and 5). Cellular DNA prepared from samples containing test articles that were spiked with $10^2$ $TCID_{50}$ RAV1 irradiated prior to plating (FIG. 3; lanes 6 and 7) and test articles without a spike (FIG. 3; lanes 8 and 9) were negative for these specific proviral sequences confirming the absence of replicating ALV-like virus in the test articles. DNA prepared from uninfected cultures (FIG. 3; lanes 10 and 11) were negative indicating no cross reactivity of the primer pairs with germline ALV (ev) loci. To control for the integrity of the DNA in the expected negative ALV specific PCR results from test articles without spikes, we used a specific PCR assay for the amplification of the highly redundant EAV0 loci present in all CEF cells. All samples (2–11) were positive indicating all samples had amplifiable genomic EAV0 specific sequences.

The foregoing descriptions of the various embodiments of the invention have been presented for purposes of illustration and description. They are not intended to be exhaustive or to limit the invention to the precise form disclosed, and many obvious modifications and variations by those skilled in the art are possible in light of the above teaching.

REFERENCES

[1] American Academy of Pediatrics. Combination vaccines for childhood immunization: Recommendations of the Advisory Committee on Immunization Practices (ACIP), the American Academy of Pediatrics (AAP) and the American Academy of Family Physicians (AFP). Pediatrics. 1999; 103:1064–1068.

[2] Limbach K J, Paoletti E. Non-replicating expression vectors: applications in vaccine development and gene therapy. Epidemiol. Infect. 1996; 116: 241–56.

[3] Tartaglia J, Paoletti E. Live recombinant viral vaccines. In: Van Regenmortel MHV, Neurath A R, editors. Immunochemistry of Viruses II, The basis for serodiagnosis and vaccines. New York, Elsevier, 1990: pp. 125–151.

[4] Requirements for the use of animal cells as in vitro substrates for the production of biologicals. In: WHO Expert Committee on Biological Standardization; Requirements for Biological Substances, No. 50. Geneva, World Health Organization, 1998, Annex 1, WHO Technical Report Series, No. 878. 1998, pp. 19–56.

[5] Silver J, Maudru T, Kazunobu F, and Repaske R. An RT-PCR assay for the enzyme activity of reverse transcriptase capable of detecting single virions. Nucleic Acids Research 1993; 21: 3593–94.

[6] Pyra H, Boni J, and Schupbach J. Ultrasensitive retrovirus detection by a reverse transcriptase assay based on product enhancement. Proc. Natl. Acad. Sci. 1994: 51: 1544–48.

[7] Heneine W. Yamamoto S, Switzer W M, Spira T J, folks T M. Detection of reverse transcriptase by a highly sensitive assay in sera from persons infected with human immunodeficiency virus type1. J. Infect. Dis. 1995; 171: 1210–6.

[8] Boni J, Stalder J, Reigel F, Schupbach J. Detection of reverse transcriptase activity in live attenuated virus vaccines. Clin. Diag. Virol. 1996; 5: 43–53.

[9] Maudru T, Peden K W. Analysis of a coded panel of licensed vaccines by polymerase chain reaction-based reverse transcriptase assays: a collaborative study. J Clin. Virol. 1998; 11: 19–28.

[10] Kahn A S. Maudru T, Thompson A, Muller J, Sears J F, Peden K W. The reverse transcriptase activity in cell-free medium of chicken embryo fibroblasts cultures is not associated with a replication-competent retrovirus. J. Clin. Virol. 1998; 11: 7–18.

[11] Robertson J S, Minor P. Reverse transcriptase activity in vaccines derived from chick cells. Biologicals. 1996; 24: 289–90.

[12] Tsang S X, Switzer W M, Shanmugam V, Johnson J A, Goldsmith C, Wright A, Fadly A, Thea D, Jaffe H, Folks T M, Heneine W. Evidence of avian leukosis virus subgroup E and endogenous avian virus in measles and mumps vaccines derived from chicken cells: investigation of transmission to recipients. J. Virol. 1999; 73: 5843–51.

[13] Bauer G, Friis R R, Jilek G, Hofschneider P H. Purification and characterization of particles containing RNA-dependent DNA polymerase, in the allantoic fluid of uninfected leukosis virus-free chicken eggs. Biochim Biophy. Acta. 1978; 518: 125–37.

[14] Bauer G, Jilek G, Hofschneider P H. Purification and further characterization of an RNA-dependent DNA polymerase from the allantoic fluid of leukosis-virus-free chicken eggs. Eur. J. Biochem. 1977; 79: 345–54.

[15] Bauer G, Hofschneider P H. An RNA-dependent DNA polymerase, different from the known viral reverse transcriptases, in the chicken system. Proc. Natl. Acad. Sci. 1976; 73: 3025–9.

[16] Purchase G H, Payne L N. Leukosis/Sarcoma Group. In: Hofstad M S, Barnes J H, Calnek B W, Reid W M, Yoder H W, editors. Diseases of Poultry Eight Edition. Iowa State Press, 1984 pp. 360–405.

[17] Boyce-Jacino M T, O'Donoghue K, Faras A J. Multiple complex families of endogenous retroviruses are highly conserved in the genus Gallus. J. Virol. 1992; 66: 4919–29.

[18] Resnick R M, Boyce-Jacino M T, Fu Q, Faras A J. Phylogenetic distribution of the novel avian endogenous provirus family EAV-0. J. Virol. 1990; 64: 4640–53.

[19] Dunwiddle C T, Resnick R, Boyce-Jacino M, Alegre J N, Faras A J. Molecular Cloning and Characterization of gag-, pol-, and env-related gene sequences in the ev-chicken. J. Virol. 1986; 59: 669–75.

[20] Dunwiddie C, Faras A J. Presence of retrovirus reverse transcriptase-related gene sequences in avian cells lacking endogenous avian leukosis viruses. Proc. Natl. Acad. Sci. 1985; 82; 5097–101.

[21] Weissmhar R N, Schupbach J, Boni J. Reverse Transcriptase Activity in Chicken Emybryo Fibroblasts Culture Supernatants Is associated with Particles Containing Endogenous Avian Retrovirus EAV-0 RNA. J. Virol. 1997; 71: 3005–12.

[22] Robertson J S, Nicolson C, Riley A-M, Bentley M, Dunn G, Corcoran T, Schild GC, Minor P. Assessing the significance of reverse transcriptase activity in chick-derived vaccines. Biologicals 1997; 25: 403–14.

[23] Fry M. and Loeb L. A. Animal Cell DNA Polymerases. CRC Press Boca Raton, 1986.

[24] Jones, M D. and Foulkes, N S. Reverse transcription of mRNA by Thermus aquaticus DNA polymerase. Nucleic Acids Res. 1989; 17: 8387–8.

[25] Maudru T, Peden K. Elimination of background signals in a modified polymerase chain reaction-based reverse transcriptase assay. J. Virol. Methods. 1997; 66: 247–61.

[26] Chang A, Ostrove J M, Bird R E. Development of an improved product enhanced reverse transcriptase assay. J. Virol. Methods. 1997; 65: 45–54.

[27] Lugert R, Konig H, Kurth R, Tonjes R R. Specific suppression of false-positive signals in the product-enhanced reverse transcriptase assay. Biotechniques. 1996; 20: 210–17.

[28] Astrin S M, Buss E G, Haywards W S. Endogenous viral genes are non-essential in the chicken. Nature (London). 1979; 282: 339–41.

[29] Coffin J M, Tsichlis P N, Conklin K F, Senior A, Robinson H L. Genomes of endogenous and exogenous avian retroviruses. Virology. 1983; 126: 51–72.

[30] Waters T D, Anderson P S Jr, Beebe G W, Miller R W. Yellow fever vaccination, avian leukosis virus, and cancer risk in man. Science. 1972; 177: 76–77.

We claim:

1. A method for detecting the presence of greater than or equal to a pre-selected level of infectious retrovirus in a biological sample, the method comprising:
   a) conducting a PCR-based reverse transcriptase (PBRT) assay on a sample of a cellular substrate permissive to retrovirus infection and determining the minimum number of PCR cycles in the PBRT assay necessary to detect endogenous reverse transcriptase activity in the cellular substrate;
   b) co-culturing a known quantity of a known replication competent virus with another sample of the same cellular substrate, subjecting the replication competent virus to an initial transmissibility assay to amplify the replication competent virus, and determining the transmissibility assay parameters that amplify infectious retrovirus at the pre-selected level in the cellular substrate to a level detectable in a PBRT assay using fewer than the minimum number of PCR cycles necessary to detect endogenous reverse transcriptase activity in the cellular substrate as determined in a);
   c) co-culturing the biological sample with another sample of the same cellular substrate and subjecting the biological sample to a transmissibility assay employing the parameters determined in b) to yield an amplified biological sample;
   d) subjecting the amplified biological sample from c) to a PBRT assay employing fewer than the minimum number of PCR cycles necessary to detect endogenous reverse transcriptase activity in the cellular substrate;
   e) observing whether a PCR product is present in the amplified biological sample, wherein the presence of PCR product is indicative of a level of infectious retrovirus in the biological sample greater than or equal to the pre-selected level.

2. The method according to claim 1 wherein the cellular substrate is from an avian species.

3. The method according to claim 1 wherein the cellular substrate is chicken embryo fibroblasts.

4. The method according to claim 2 wherein the number of PCR cycles in the PBRT assay is from 24–26.

5. A method for detecting the presence of greater than or equal to a pre-selected level of an infectious retrovirus in a biological sample, the method comprising:
   a) co-culturing the biological sample with a cellular substrate permissive of retroviral infection under conditions that permit retrovirus amplification, wherein infectious retrovirus present in the biological sample is amplified to yield a level of infectious retrovirus RT activity greater than endogenous, non-infectious retrovirus RT activity of the cellular substrate;
   b) subjecting the co-culture to a PCR-based reverse transcriptase (PBRT) assay, wherein a number of PCR cycles is employed that is equal to or greater than the number required for detection of the exogenous, infectious RT activity in the co-culture but fewer than the number required for detection of the endogenous, non-infectious RT activity in the cellular substrate;
   c) observing whether a PCR-amplified nucleic acid is present in the co-culture subjected to the PBRT assay, wherein the presence of a PCR-amplified product is indicative of a level of infectious retrovirus in the biological sample greater than or equal to the pre-selected level.

6. The method according to claim 5 wherein the cellular substrate is from an avian species.

7. The method according to claim 5 wherein the cellular substrate is chicken embryo fibroblasts.

8. The method according to claim 6 wherein the number of PCR cycles in the PBRT assay is from 24–26.

9. In a method for the detection of reverse transcriptase activity in a biological sample using a PCR-based reverse transcriptase (PBRT) assay, the improvement comprising:

a) before conducting the PBRT assay, co-culturing the biological sample with a cellular substrate and amplifying infectious retroviruses in the biological sample to a level that is above the endogenous RT level;

b) conducting the PBRT assay on the amplified product of (a) using a number of PCR cycles that is fewer than necessary to detect endogenous reverse transcriptase activity in the cellular substrate and equal or greater than required to detect amplified exogenous, infectious reverse transcriptase activity.

10. The method according to claim 9 wherein the cellular substrate is from an avian species.

11. The method according to claim 9 wherein the cellular substrate is chicken embryo fibroblasts.

12. The method according to claim 11 wherein the number PCR cycles in the PBRT assay is from 24–26.

* * * * *

SEQUENCE LISTING

<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:
    Oligonucleotide primer

<400> SEQUENCE: 1
gtagtgccac tgtttcgttt tg                                          22

```
<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 2
ctctgcaatg cggaattcag tggt                                      24

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 3
agggggaaat gtagtcttat gcaat                                     25

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 4
atactcttgt agtcttgcaa catg                                      24

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 5
catactgagc caatggttgt aaagggca                                  28

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 6
aatgttgtat cgaaatacta cgg                                       23

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 7
ttcagtccgg accctacc                                             19
```

-continued

```
<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 8
ataggcgtga tcggggtctc gggatg                                          26

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 9
agcctgcggc ttggccaaat accg                                            24

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 10
tcctgctcaa cttcctgtcg ag                                              22
```